(12) United States Patent
Niznick

(10) Patent No.: US 9,452,028 B1
(45) Date of Patent: Sep. 27, 2016

(54) EXTERNALLY-THREADED, EXTERNALLY MICRO-GROOVED, ENDOSSEOUS DENTAL IMPLANTS

(76) Inventor: Gerald A. Niznick, Las Vegas, NV (US)

( * ) Notice: Subject to any disclaimer, the term of this patent is extended or adjusted under 35 U.S.C. 154(b) by 671 days.

(21) Appl. No.: 12/924,954

(22) Filed: Oct. 7, 2010

(51) Int. Cl.
*A61C 8/00* (2006.01)

(52) U.S. Cl.
CPC .................................. *A61C 8/0022* (2013.01)

(58) Field of Classification Search
USPC ................................................ 433/172–176
See application file for complete search history.

(56) References Cited

U.S. PATENT DOCUMENTS

| 2006/0172258 A1* | 8/2006 | Niznick ......................... 433/174 |
| 2008/0254411 A1* | 10/2008 | Bondar ......................... 433/174 |
| 2008/0280255 A1* | 11/2008 | D'Alise ........................ 433/174 |
| 2009/0233256 A1* | 9/2009 | Schroering .................... 433/174 |
| 2010/0055645 A1* | 3/2010 | Mullaly et al. ................ 433/174 |

* cited by examiner

*Primary Examiner* — Nicholas Lucchesi
*Assistant Examiner* — Matthew Saunders
(74) *Attorney, Agent, or Firm* — Patrick Bright

(57) ABSTRACT

An externally-threaded, endosseous dental implant includes an elongated body that is straight or tapered, and that includes external, distal regular threads, external micro-threads proximal to the regular threads, and external micro-grooves proximal to the micro-threads, with an internal passage in the body of the implant, the passage including internal threads, or internal multi-sided adaptor-engaging surfaces, or both.

11 Claims, 4 Drawing Sheets

EXTERNALLY-THREADED, EXTERNALLY MICRO-GROOVED, ENDOSSEOUS DENTAL IMPLANTS

This invention relates to endosseous, one-piece or two-piece, straight or tapered externally threaded implants having an externally micro-grooved region surgically placed at or below the crest of a patient's jawbone. Distal to the micro-grooved region is a micro-threaded region and distal to the micro-threaded region is a second threaded region having threads 50-75% deeper and wider spaced than the micro-threads.

These threads may, but need not be, multiple lead threads. Inside these implants is an internal passage with internal threads, and one or more wrench-engaging regions/surfaces. These implants may also include a bevel or chamfer at or near the opening to the internal passage. This bevel or chamfer may be inside the internal passage or outside the passage, at or near the opening into the passage.

The micro-grooves may be from 2 to 10 in number, may have any desired configuration, may have a depth in the range of from about 10 microns to about 60 microns, and may have a width in the range from about 50 to about 150 microns.

The micro-threads may have uniform pitch and depth, and a peak-to-valley depth in the range of about 0.1 to about 0.3 mm. The body threads may also have uniform pitch and depth, and a peak-to-valley depth of at least about 0.4 mm. At the transition point from micro-threads to body/regular threads, the peak-to-valley size of the micro-threads is preferably about 25% to about 50% of the body/regular threads, and this percentage may decrease as the body threads extend farther from this transition point.

These implants include an internal passage with an opening into the passage on the proximal end of the implant. This internal passage may terminate inside the implant. Inside of, and at or near the proximal end of the passage may be an internal, circumferential, bevel or chamfer. Distal to this bevel/chamfer, if any, and distal to the opening into the internal passage, is a multi-sided, e.g., a three, four, six or eight-sided, adaptor-engaging region/surface. This multi-sided surface permits insertion of an abutment with a complementary multi-sided distal projection into this adaptor-engaging region/surface in a plurality of positions.

A tool with a multi-sided projection at its distal end may be inserted into the multi-sided figure inside the implant for turning or twisting the implant into, or out of, a jawbone opening for the implant.

These endosseous implants comprise an elongated, externally-threaded body, that may be tapered over at least part of its length, and, optionally, an external, distal, self-tapping feature. The proximal end of these implants may comprise a flat or tapered upper surface with an opening to an internal passage that may include one or two wrench-engaging surfaces/regions, and a threaded region.

The external threads on the body of these implants may be a single, continuous, thread, or multiple lead threads, e.g., double or triple lead threads on the distal external surface. These threads may be, for example, V-shaped, buttress-shaped, square-shaped, or some other shape. A proximal region of the threaded external body may also comprise multiple lead threads, with twice the number of leads as the distal region, e.g., quadruple lead threads in the proximal region, with double lead threads in the distal region, or six lead threads in the proximal region, with triple lead threads in the distal region, where each thread may have the same pitch. Preferably, all threads have substantially the same pitch, with the distance between adjacent threads in the proximal region preferably about half the distance between adjacent threads in the distal region.

The linear length of the proximal region with its micro-grooves is preferably not more than about one-third the linear length of the body. The linear length of the distal region with micro-threads and regular threads is preferably not more than about two-thirds the linear length of the body.

As an example, with V-shaped threads, the pitch of the threads may be, for example, 1.2 mm, with the distance between adjacent quadruple lead threads about 0.3 mm in the proximal region, and about 0.6 mm between double lead threads in the distal region. With buttress/flat-based threads, the threads may have a pitch of about 1.6 mm with the distance between adjacent quadruple lead threads about 0.4 mm in the proximal region, and about 0.8 mm between double lead threads in the distal region. In such embodiments, the threads in the proximal region may start every 90°, and every 180° in the distal region.

The body of the implant may be substantially straight, or may taper. If tapering, the taper may extend distally over more than 50% of the implant's linear length, over at least about 30% of the linear length of the body in some embodiments, and over at least about 50% of the linear length of the body in some embodiments, such that the crest of substantially all the peaks in the distal region are not on an axial plane parallel to the longitudinal axis of the implant. For example, the proximal externally-threaded body region may be untapered, and comprise up to about 65% of the linear length of the body, but the distal, externally-threaded region of the implant body may taper about 35% of the linear length of the body.

In some embodiments, e.g., tapered implants with double lead threads in the distal region and quadruple lead micro-threads in the proximal region, the trough/valleys between adjacent peaks of the proximal threads are approximately 0.2 mm in depth and 0.4 mm in depth for the distal threads.

As these implants are threaded or screwed into an opening in the jawbone of a patient, the multiple lead threads on the distal surface of the implant body enter and cut threads in the opening. When the multiple lead threads on the proximal region of the implant body enter this opening, the implant can continue to be threaded, without cross threading, into threads already formed inside the opening.

For example, where the distal region of the implant body includes double lead threads, two of the quadruple lead threads follow the threads created and formed in bone by the double lead threads. The other two threads in the proximal region that are located between the two threads that follow the double lead proximal threads, either cut their way into the bone between the threads, or bypass the existing threads, but do not cut across threads formed in the bone cavity by the double lead threads.

As an additional example, with triple lead threads at the distal region, and six threads starting every 60° in the proximal region, three of the triple lead threads in the six-thread region follow the threads created in bone by the triple lead threads, and the other three threads cut their way into the bone between the threads formed by the triple lead thread region, or are positioned without disturbing the threads already formed.

These implants may also include one or more of the features of the endosseous dental implants, abutments and other related products, disclosed in the following U.S. Patents and Patent Applications:

Externally-Threaded Endosseous Dental Implants With Internal Abutment Engaging And Fixture Mount Engaging Surfaces, US published patent number 2006/0172257 A1;

One-Piece, Screw-Receiving, Externally-Threaded Endosseous Dental Implants And Related Transfer Components, Comfort Caps And Abutments, US published patent number 2006/0183078 A1;

U.S. Pat. No. 7,108,510, issued Sep. 19, 2006, and entitled "Endosseous Dental Implant";

U.S. published patent application 2006/0003290, entitled "Endosseous One-Piece Screw-Type Dental Implants";

U.S. Pat. No. 7,014,464, issued Mar. 21, 2006, and entitled "Multi-part Abutment And Transfer Cap For Use With An Endosseous Dental Implant With Non-Circular, Beveled Implant Abutment Interface"; and U.S. Pat. No. 4,960,381, issued Oct. 2, 1990, entitled "Screw-Type Dental Implant Anchor

BRIEF DESCRIPTION OF THE DRAWINGS

These endosseous dental implants with external threads, micro-threads and micro-grooves can better be understood by reference to the drawings, which are provided only as examples, and not as definitions of any term in the claims, and in which:

DETAILED DESCRIPTION OF THE DRAWINGS

Figure 1:
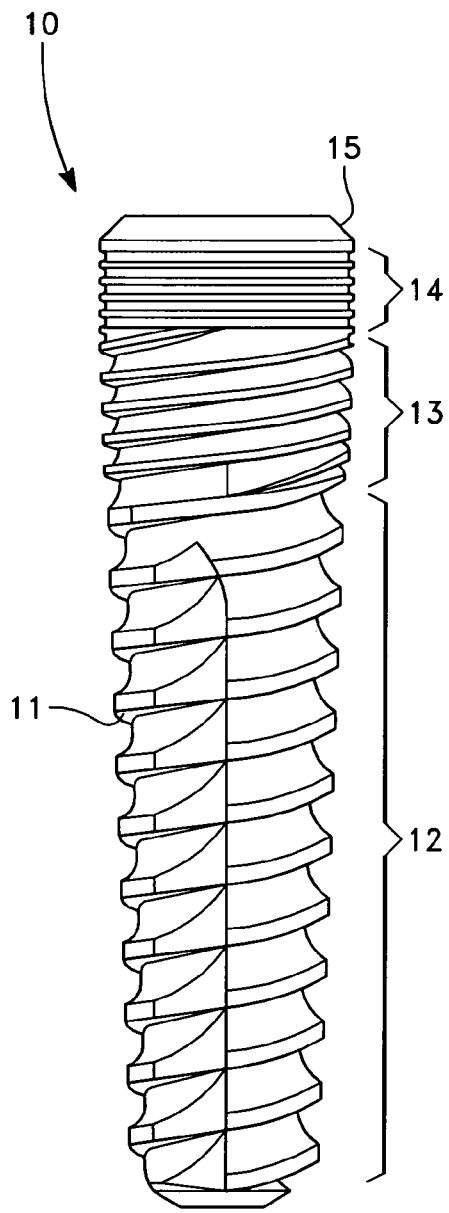
FIG. 1 shows a side elevation view of a tapered endosseous dental implant with a tapered, externally-threaded body that includes micro-grooves in the proximal region of the external sidewall of the implant, and in the distal region, micro-threads and regular threads, and an internal, multi-sided implant adaptor/abutment-engaging region.
Figure 2:
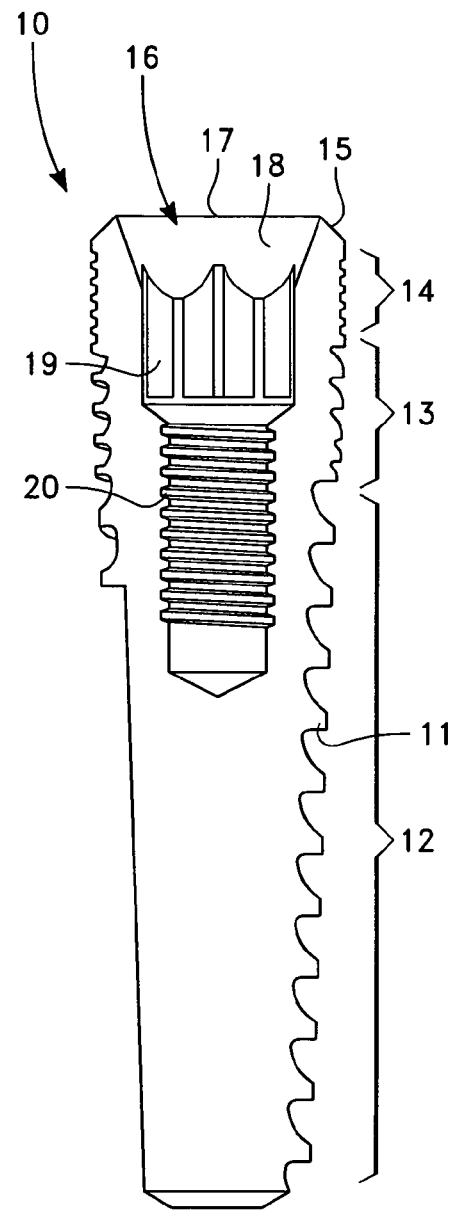
FIG. 2 is a side elevation view in vertical cross section of the implant of FIG. 1, showing the internal passage inside the implant, and near the opening into this passage, an internal, multi-sided implant adaptor/abutment-engaging region.

FIGS. 1 and 2 show a tapered endosseous dental implant 10 in side elevation and cross-sectional side elevation views, respectively. Implant 10 includes tapered body 11. Body 11 includes two distal externally-threaded regions 12 and 13. Externally-threaded region 12 includes several regular threads, all of which have the same shape/pitch, and externally-threaded region 13 includes three or four micro-threads, all of which have the same shape/pitch. Proximal external body region 14 comprises a plurality of micro-grooves, e.g., three such grooves. Spacing between adjacent threads is substantially the same.

Tapered top surface 15 lies just above region 14, and atop dental implant 10. Region 13 comprises about 30% of the linear length of body 11. Body 11 tapers about 50% from the proximal end of portion 13 to its distal end.

Inside implant 10 is internal passage 16. Passage 16 terminates inside tapered body 11, and includes an opening 17 that lies in flat top surface 15. Near opening 17 and in passage 16 is downwardly- and inwardly-tapering circumferential chamfer 18. Distal to chamfer 18 is multi-sided-sided adaptor-engaging surface/region 19. Distal to region 19 are internal threads 20, suitable for engaging the threaded shank of an adaptor or of a screw that holds an adaptor atop implant 10.

Spacing between adjacent external threads and grooves is substantially the same. Distal portion 13 comprises about 30% of the linear length of body 11. Body 11 tapers about 50% from the proximal end of portion 13 to its distal end.

Figure 3:
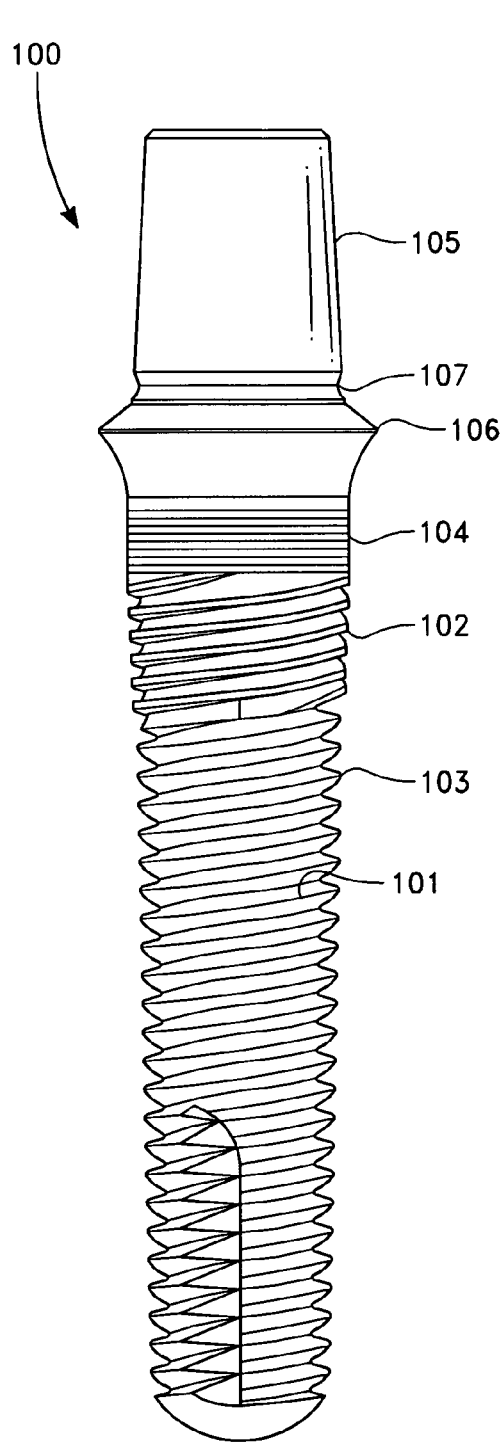
FIG. 3 shows a side elevation view of a tapered endosseous dental implant with a tapered, externally-threaded body that includes proximal, integrally-formed abutment and outwardly-flaring, unthreaded portions; and, in distal succession, micro-grooves in the proximal region of the external sidewall of the implant, and in the distal region, micro-threads and regular threads, and an internal, multi-sided implant adaptor/abutment-engaging region.
Figure 4:
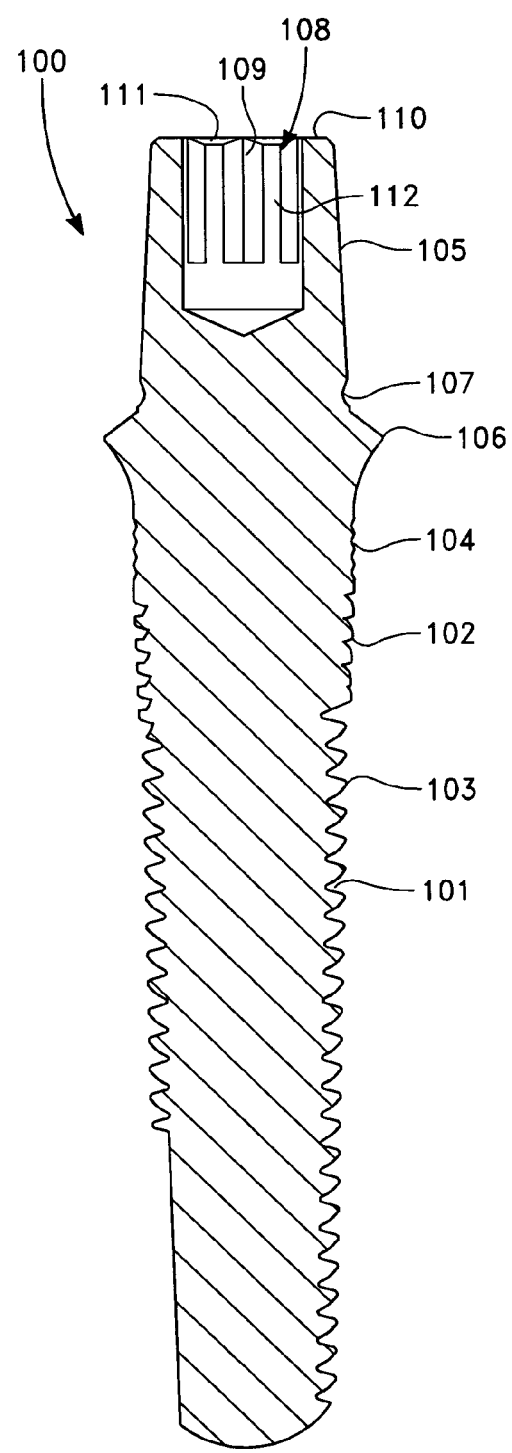
FIG. 4 is a side elevation view in vertical cross section of the implant of FIG. 3, showing an internal passage inside the implant, and near the opening into this passage, an internal, multi-sided implant adaptor/abutment-engaging region.

FIGS. 3 and 4 show a tapered endosseous dental implant 100 in side elevation and cross-sectional side elevation views, respectively. Implant 100 includes tapered body 101. Body 101 includes two distal externally-threaded regions 102 and 103. Externally-threaded region 103 includes several regular threads, all of which have the same shape/pitch, and externally-threaded region 102 includes three or four micro-threads, all of which have the same shape/pitch. Proximal external body region 104 comprises a plurality of micro-grooves, e.g., six such grooves. Spacing between adjacent threads is substantially the same. The size and shape of all grooves is substantially the same.

Atop, and proximal to region 104 is outwardly-flaring, unthreaded region 106, integrally formed with implant 100. Frusto-conical, distally-tapering, external abutment portion 105 is integrally-formed atop implant 100, and includes distally-formed, circumferential undercut 107.

Inside implant 100 is internal passage 108. Passage 108 terminates inside abutment portion 105, and includes an opening 109 that lies in flat top surface 110. Near opening 109 and in passage 108 is downwardly- and inwardly-tapering circumferential chamfer 112.

Spacing between adjacent external threads and grooves is substantially the same. Distal portion 101 comprises about 65% of the linear length of body 101.

Figures 5, 6:
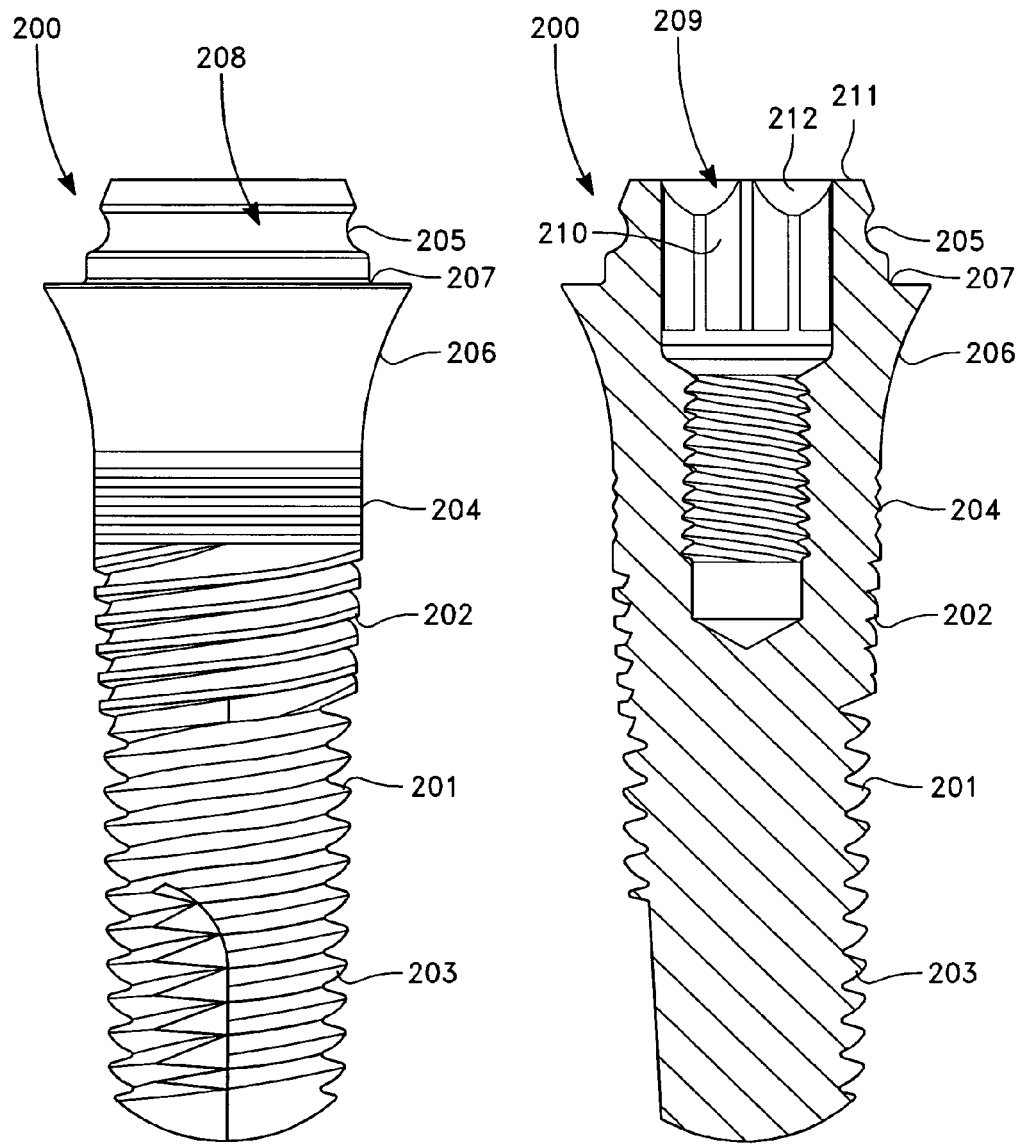
FIG. 5 shows a side elevation view of a tapered endosseous dental implant with a tapered, externally-threaded body that includes proximal, integrally-formed abutment and outwardly-flaring, unthreaded portions; and, in distal succession, micro-grooves in the proximal region of the external sidewall of the implant, and in the distal region, micro-threads and regular threads; and an internal passage that includes proximal internal, multi-sided implant adaptor/abutment-engaging region, and distal internal threads.
FIG. 6 is a side elevation view in vertical cross section of the implant of FIG. 5, showing the internal passage inside the implant, and near the opening into this passage, a proximal, internal, multi-sided implant adaptor/abutment-engaging region, and a distal, internal threaded region.

FIGS. 5 and 6 show a tapered endosseous dental implant 200 in side elevation and cross-sectional side elevation views, respectively. Implant 200 includes tapered body 201.

Body 201 includes two distal externally-threaded regions 202 and 203. Externally-threaded region 203 includes several regular threads, all of which have the same shape/pitch, and externally-threaded region 202 includes five or six micro-threads, all of which have the same shape/pitch. Proximal external body region 204 comprises a plurality of micro-grooves, e.g., six such grooves. Spacing between adjacent threads is substantially the same. The size and shape of all grooves is substantially the same.

Atop, and proximal to region 204 is outwardly-flaring, unthreaded region 206, integrally formed with implant 100. Frusto-conical, distally-tapering, external abutment portion 205 is integrally-formed atop implant 200, and includes distally-formed, circumferential undercut 207, and sidewall circumferential groove.

Inside implant 200 is internal passage 209. Passage 209 terminates inside abutment portion 205, and includes an opening 210 that lies in flat top surface 211. Near opening 210 and in passage 209 is downwardly- and inwardly-tapering circumferential chamfer 212.

Spacing between adjacent external threads and grooves is substantially the same. Distal portion 203 comprises about 65% of the linear length of body 201.

Figure 7:
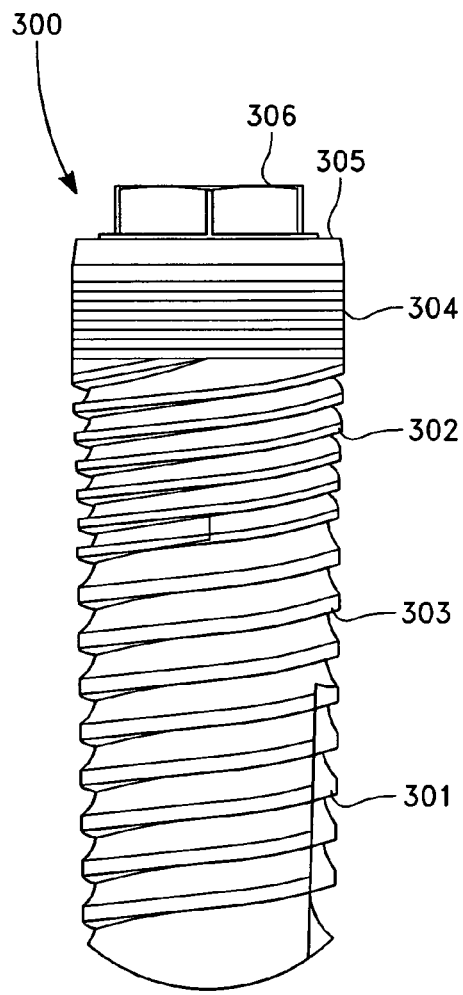
FIG. 7 shows a side elevation view of a tapered endosseous dental implant with a tapered, externally-threaded body that includes, in distal succession, an external, multi-sided, here six-sided, external wrench-engaging portion, micro-grooves in the proximal region of the external sidewall of the implant, and in the distal region, micro-threads and regular threads; and an internal passage that includes proximal internal threads.
Figure 8:
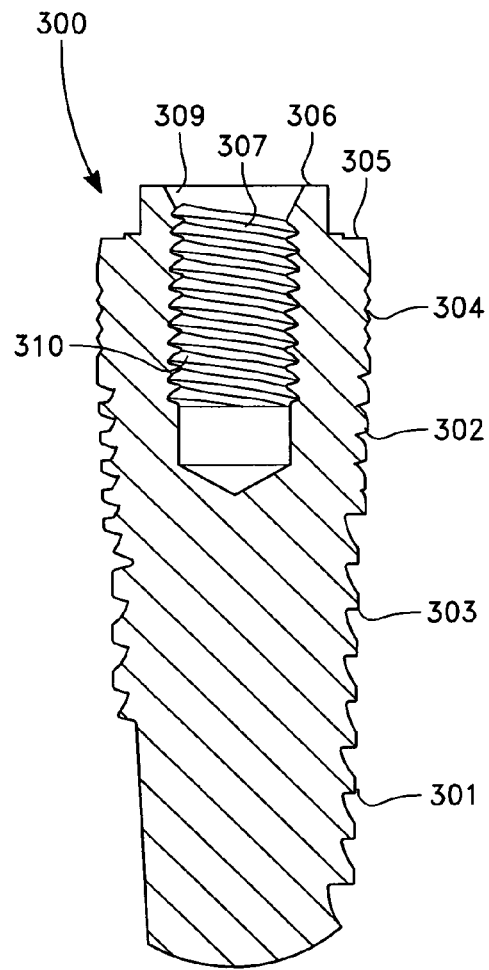
FIG. 8 is a side elevation view in vertical cross section of the implant of FIG. 7, showing the internal passage inside the implant, and near the opening into this passage, a proximal, internal, threaded region.

FIGS. 7 and 8 show a tapered endosseous dental implant 300 in side elevation and cross-sectional side elevation views, respectively. Implant 300 includes tapered body 301. Body 301 includes two distal externally-threaded regions 302 and 303. Externally-threaded region 303 includes several regular threads, all of which have the same shape/pitch, and externally-threaded region 302 includes five or six micro-threads, all of which have the same shape/pitch. Proximal external body region 304 comprises a plurality of micro-grooves, e.g., six such grooves. Spacing between adjacent threads is substantially the same. The size, spacing and shape of all grooves is substantially the same.

Atop, and proximal to region 304 is substantially flat upper surface 305, integrally formed atop implant 300. Atop flat surface 305 is multi-sided, wrench-engaging, external portion 306, integrally-formed atop surface 305.

Inside implant 300 is internal passage 307. Passage 307 terminates inside implant body 301, and includes an opening 308 that lies in portion 306. Near opening 308 and in passage 307 is downwardly- and inwardly-tapering circumferential chamfer 309. Distal to chamfer 309 is internally-threaded region 310.

Spacing between adjacent external threads and grooves is substantially the same. Distal portion 303 comprises about 65% of the linear length of body 301.

The implant may be made of commercially-pure titanium, a titanium alloy, or both, and may have an outside diameter in the range of about 3 to about 7 millimeters. The implant may have a length in the range of about 6 to about 18 millimeters.

The invention claimed is:

1. An endosseous dental implant, comprising an elongated, externally-threaded body having a top surface, straight or tapered over at least part of its length, and, distal to, and close to said top surface, and, adapted to engage bone, a plurality of horizontal, contiguous microgrooves in a micro-grooved region, with a micro-threaded region distal to the micro-grooved region, and a regular threaded region distal to the micro-threaded region; and an internal passage in the body of said implant, said passage having an opening at the top of said implant, said passage including internal threads, and internal wrench-engaging surfaces, said passage terminating inside said dental implant.

2. The dental implant of claim 1, further comprising at least two external regions of multiple lead threads, including a distal region comprising double lead threads, and a proximal region comprising quadruple lead threads, wherein said proximal region is shorter than said distal region.

3. The dental implant of claim 2, wherein said proximal region is less than half the linear length of the distal region.

4. The dental implant of claim 1 wherein a number of micro-grooves in said microgrooved region is in the range of two to ten, the width of the micro-grooves is in the range of about 50 to about 150 microns, and the depth of the micro-grooves is in the range of about 10 to about 40 microns.

5. The dental implant of claim 1, further comprising at least two external regions of multiple lead threads, including a distal region comprising triple-lead threads, and a proximal region comprising six-lead threads, wherein said proximal region is shorter than said distal region.

6. The dental implant of claim 1, wherein said proximal region is less than half the linear length of the distal region.

7. The dental implant of claim 1, wherein said body tapers over at least about 35% of its linear length.

8. The dental implant of claim 1 further comprising a chamfered internal surface inside of, and near to the opening into said passage.

9. The dental implant of claim 1 wherein said internal threads are below an internal multi-sided adaptor-engaging surfaces.

10. The dental implant of claim 1 wherein said passage is adapted to receive and engage an adaptor selected from the group consisting of cementable adaptors and threaded adaptors.

11. An endosseous dental implant, comprising an elongated, externally-threaded body having a top surface, straight or tapered over at least part of its length, and, in distal succession from said top surface, a frusto-conical abutment portion integrally formed on said implant, an unthreaded, outwardly-flaring region, and close to said unthreaded, outwardly-flaring region, and, adapted to engage bone, a plurality of horizontal, contiguous micro-grooves in a micro-grooved region, with a micro-threaded region distal to the micro-grooved region, and a regular threaded region distal to the micro-threaded region; and an internal passage in the body of said implant, said passage having an opening at the top of said implant, said passage including internal wrench-engaging surfaces, said passage terminating inside said dental implant.

* * * * *